(12) United States Patent
Wassertheurer et al.

(10) Patent No.: US 8,920,327 B2
(45) Date of Patent: Dec. 30, 2014

(54) METHOD FOR DETERMINING CARDIAC OUTPUT

(75) Inventors: Siegfried Wassertheurer, Bad Gleichenberg (AT); Christopher Mayer, Steingasse (AT)

(73) Assignee: ARC Seibersdorf Research GmbH, Vienna (AT)

( * ) Notice: Subject to any disclaimer, the term of this patent is extended or adjusted under 35 U.S.C. 154(b) by 1579 days.

(21) Appl. No.: 12/084,668

(22) PCT Filed: Nov. 8, 2006

(86) PCT No.: PCT/AT2006/000457
§ 371 (c)(1),
(2), (4) Date: Nov. 21, 2008

(87) PCT Pub. No.: WO2007/053868
PCT Pub. Date: May 18, 2007

(65) Prior Publication Data
US 2009/0287095 A1    Nov. 19, 2009

(30) Foreign Application Priority Data
Nov. 8, 2005   (AT) .................. A 1818/2005

(51) Int. Cl.
*G06F 19/00* (2011.01)
*A61B 5/021* (2006.01)
*A61B 5/029* (2006.01)
*A61B 5/00* (2006.01)

(52) U.S. Cl.
CPC .............. *A61B 5/021* (2013.01); *A61B 5/029* (2013.01); *G06F 19/345* (2013.01); *G06F 19/363* (2013.01); *A61B 5/7264* (2013.01); *A61B 5/7267* (2013.01)
USPC ....................................... 600/485

(58) Field of Classification Search
USPC ................ 128/925; 600/408; 700/48
See application file for complete search history.

(56) References Cited

U.S. PATENT DOCUMENTS 5,339,818 A * 8/1994 Baker et al. ............ 600/490
5,400,793 A   3/1995 Wesseling
(Continued)

FOREIGN PATENT DOCUMENTS

WO   WO 92/12669        8/1992
WO   WO 9212669 A1 *    8/1992

OTHER PUBLICATIONS

Wesseling, K.H., et al., Computation of Aortic Flow from Pressure in Humans Using a Nonlinear, Three-Element Model, Journal of Applied Physiology, vol. 74, No. 5, May 1993, pp. 2566-2573.
Siebenhofer, A., et al., The Reproducibility of Central Aortic Blood Pressure Measurements in Healthy Subjects Using Applanation Tonometry and Sphygmocardiography, Journal of Human Hypertension, vol. 13, No. 9, Sep. 1999, pp. 625-629.
(Continued)

*Primary Examiner* — Melanie Y Brown
*Assistant Examiner* — Erik B Crawford
(74) *Attorney, Agent, or Firm* — Taft Stettinius & Hollister LLP

(57) ABSTRACT

In a method for determining cardiac output from an arterial blood pressure curve measured at the periphery, in which the blood pressure curve measured at the periphery is arithmetically transformed into the corresponding central blood pressure curve and the cardiac output is calculated from the central blood pressure curve, the transformation of the blood pressure curve measured at the periphery into the corresponding central blood pressure curve is performed by the aid of an artificial neural network whose weighting values are determined by learning.

10 Claims, 2 Drawing Sheets

(56) References Cited

U.S. PATENT DOCUMENTS

| | | |
|---|---|---|
| 5,533,511 A | 7/1996 | Kaspari et al. |
| 6,186,955 B1 | 2/2001 | Baura |
| 2002/0028998 A1 | 3/2002 | Chesney et al. |
| 2004/0181145 A1* | 9/2004 | Al Bandar et al. ............ 600/408 |

OTHER PUBLICATIONS

Bogert. L.W.J, et al., Non-Invasive Pulsatile Arterial Pressure and Stroke Volume Changes from the Human Finger, Experimental Physiology, vol. 90, No. 4, Jul. 2005, pp. 437-446.

* cited by examiner

METHOD FOR DETERMINING CARDIAC OUTPUT

The invention relates to a method for determining cardiac output from an arterial blood pressure curve measured at the periphery, in which the blood pressure curve measured at the periphery is arithmetically transformed into the corresponding central blood pressure curve and the cardiac output is calculated from the central blood pressure curve, as well as the corresponding device.

There are numerous ways to determine cardiac output. An invasive method for measuring cardiac output was described in 1870 by the German physiologist Adolf Fick and is based on the fact that the blood flow can be calculated from the quotient of the amount of a supplied substance and the concentration difference between venous and arterial vessels.

In the dilution method, the concentration is measured distally after the injection of a dye. The blood flow can be determined by a change in the concentration of the dye. To determine the cardiac output therefrom, the lung flow is measured by the aid of a central venous access and an arterial access. Besides, regular blood takings are required.

A further development was provided by the Swan-Ganz catheter, followed by the development of thermodilution which utilizes cold as an indicator. In that case, 5 to 10 ml of cold isotonic saline or dextrose solutions are injected into the right auricle and temperature fluctuations are detected via a thermistor in the pulmonary artery. The cardiac output is indirectly proportional to the surface below the curve of the temperature fluctuations. Further methods for determining cardiac output include Doppler echocardiography and the impedance method.

Another method utilizes a pulse contour technique for determining the stroke volume and cardiac output from a pressure signal measured in the human aorta. The dependence of the cardiac output, or the mean aorta flow, on the aortic pressure is, however, not linear such that the calculation must be based on relatively complex models. As a rule, a so-called windkessel model is adopted, which takes into account the fact that the aorta is subjected to an elastic expansion due to the contraction of the heart and the homogenous flow resistance in the peripheral portions of the arterial system and the thus caused pressure increase in the interior of the vessel. In that model, the aorta corresponds to a windkessel which serves to attenuate rhythmic pressure and flow fluctuations. The blood volume ejected by the heart is substantially taken up in the aorta, or windkessel, and partially flows off through the peripheral vascular regions of the different organs branching off the aorta. During the period in which the heart does not eject any blood, i.e. in the diastolic period, the elastic return of the aorta wall causes an outward flow of the aorta into the peripheral vascular regions, which again corresponds to the mode of functioning of a windkessel.

Departing from that windkessel model, an improved simulation model was proposed in U.S. Pat. No. 5,400,793, in which the aorta was assigned a transmission function and wherein an arcus-tangent function was additionally used for the dependence of the volume flow on the pressure in the aorta.

In all of the hitherto mentioned methods for determining cardiac output, invasive interventions into the human body have been necessary such that the use of those methods has been expensive and impractical and, therefore, reserved to intensive medicine. In order to avoid a pressure measurement in the aorta, U.S. Pat. No. 5,400,793 already proposed to perform such pressure measurement non-invasively in a peripheral region and, for instance, record the pressure in the Arteria radialis or brachialis. The arterial blood pressure measured at the periphery is, however, distorted as compared to the aortic pressure, thus requiring the peripheral blood pressure curve to be mapped onto a corresponding central blood pressure curve, i.e. onto the equivalent aortic pressure. Such a transformation of the blood pressure curve is, however, extremely complex, since a plurality of parameters which are responsible for the distortion of the blood pressure curve measured in the periphery will have to be taken into consideration. The transmission path between the aorta and the periphery, for instance, is characterized by its narrow-band nature and by resonance phenomena in the low-frequency range. In this context, U.S. Pat. No. 5,400,793 proposed to make an appropriate correction by an anti-resonance filter. Such a correction will, however, not consider every error influence and, in addition, result in an extremely complex and arithmetically intensive method.

The present invention aims to provide a method and a corresponding device for determining cardiac output, which, based on the arterial blood pressure curve measured at the periphery, enable the precise determination of the cardiac output, wherein computational expenditures are to be kept within reasonable limits in order to enable its integration in a mobile and accordingly handy appliance. Moreover, the back-calculation of the blood pressure curve measured at the periphery to the central blood pressure curve is to function reliably while taking into account any possible distortion occurring on the transmission path between the aorta and the peripheral region in a manner differing from one patient to another.

To solve this object, the invention essentially consists in that the transformation of the blood pressure curve measured at the periphery into the corresponding central blood pressure curve is performed by the aid of an artificial neural network whose weighting values are determined by learning. By the use of an artificial neural network, the complexity of the required transformation is accounted for in the optimum manner, and it could be proved that the central blood pressure curve obtained by said transformation actually corresponded exactly to the pressure curve each determined in the aorta at test measurements. The use of an artificial neural network provides such exact results because the underlying problem of taking into account the individual distortions of the pressure signal in the back-calculation of the peripheral blood pressure curve to the central blood pressure curve is very poorly defined and the development of an algorithmic solution is difficult. A sufficiently precise analytical model in the present case is unknown or extremely complex such that a computational determination will be very elaborate and arithmetically intensive, if possible at all. By the use of an artificial neural network, the calculation time will be substantially reduced, thus enabling the method according to the invention to be performed by the aid of a mobile device constantly ready for operation.

The corresponding device according to the invention for determining the cardiac output from the arterial blood pressure curve measured at the periphery includes a measuring device for detecting the blood pressure curve at the periphery, a calculation unit for transforming the measured blood pressure curve into the respective central blood pressure curve, and a calculation unit for calculating the cardiac output from the central blood pressure curve, wherein the calculation unit for transforming the measured blood pressure curve comprises an artificial neural network with weighting values determined by learning.

Artificial neural networks are composed of several neurons. The neurons serve to take up information from the environment or from other neurons and transmit the same to other neurons or the environment, respectively. There are three different types of neurons: input units, which are neurons capable of receiving signals from the external world; hidden units, which are neurons located between input and output neurons and including an internal representation of the external world; output units, which are neurons transmitting signals to the external world. Neurons are interconnected by edges, wherein the strength of the connection between two neurons is expressed by a weight. The higher the absolute value of the weight, the greater the influence of a neuron on the other neuron. A positive weight signifies that a neuron exerts an excitatory, exciting influence on another neuron. A negative weight implies that the influence is of inhibitory, i.e. impeding, nature. A weight of 0 means that, for the time being, a neuron does not exert any influence on another neuron. The knowledge of a neural networkis stored in these weights, weight changes between the neurons being feasible by training the network.

In the context of the present invention, it may be proceeded in a manner that the artificial neural network is trained by supervised learning. In doing so, the network, whose architecture was determined and whose weights were randomly initialized, is fed with input data during the learning process. The output of the network is compared with the set point and the weights of the network are subsequently corrected. Input and output pairs are known in advance. In order for the artificial neural network to effect a transformation of the peripheral blood pressure curve to the central blood pressure curve as exactly as possible, it is important that input data covering a wide spectrum of possible input values are used during training to avoid specialization of the network. For this reason, data sets covering the bandwidth of the potential properties should be used for training so as to enable generalization of the trained network.

In the context of the present invention, it is, therefore, preferably proceeded such that, for training the artificial neural network, respectively associated blood pressure curve pairs actually determined by measurements in the periphery or in the aorta, respectively, are used. In this respect, it is moreover crucial that measuring data from patients of different ages, sexes, constitutional types, health conditions and the like be used.

In the context of the present invention, it is, furthermore, preferably proceeded in a manner that the weighting values of the artificial neural network during supervised learning are determined by the aid of the backpropagation algorithm. The backpropagation algorithm is a numerical learning method based on the optimization of the mean squared error. Input data input into the neural network are to be mapped as precisely as possible onto the desired output data. To this end, the quality of the mapping is described by an error function mostly defined by the squared error. The backpropagation algorithm in this case will proceed in the following phases: At first, an input pattern will be established and forwardly propagated through the network. The output of the network will be compared with the desired output, with the difference of the two values being considered as an error of the network. The error will finally be propagated back to the input layer via the output layer, with the weightings of the neural connections being changed as a function of their influence on the error. This will guarantee an approximation to the desired output at a new application of the input pattern.

As already mentioned, artificial neural networks are composed of neurons, which are arranged in different layers. Between the input and the output layers, hidden layers are provided, the required number of hidden layers being limited by the respective problem. Neural networks are classified according to their topologies, the most important distinctive feature being feedbacks. Networks that have no feedback are referred to as feed-forward networks, while networks with feedback are called recurrent networks. Feed-forward networks do not comprise any path leading from a neuron, directly or via intermediately arranged neurons, back to said neuron. Hence, data are transmitted only in one direction. In the context of the method according to the invention, it is preferably proceeded in a manner that a feed-forward network, in particular a completely connected feed-forward network, is selected as said artificial neural network. Hence results a particularly simple network structure, wherein a completely connected network is a network having each neuron of a defined layer connected with each neuron of the consecutive layer. In this respect, a configuration in which the artificial neural network is comprised of at least three layers is particularly preferred, whereby, in the case of three layers, the number of neurons contained in the first and third layers are each selected to be at least three times, preferably at least five times, particularly preferred ten times, the number of neurons contained in the second, central layer. In the context of the present invention, a particularly preferred topology is configured such that, in the case of three layers, the first and the last layers of the network are each composed of at least 100 neurons and the second, central layer is composed of at least 10 neurons.

In the following, the invention will be explained in more detail by way of an exemplary embodiment schematically illustrated in the drawing. Therein, FIG. 1 is a schematic illustration of the device according to the invention;

Figure 1:
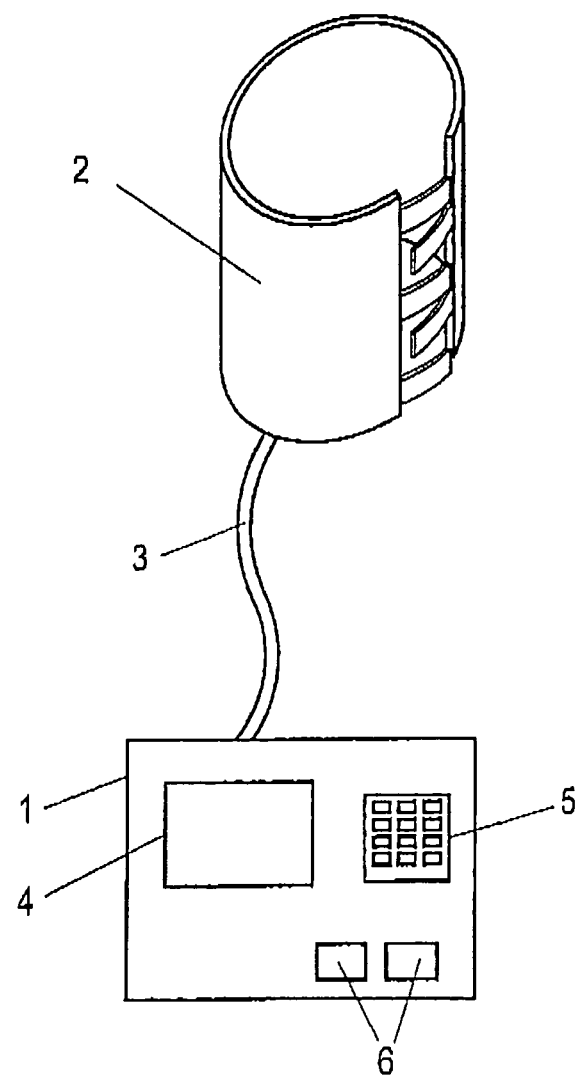
Figure 2:
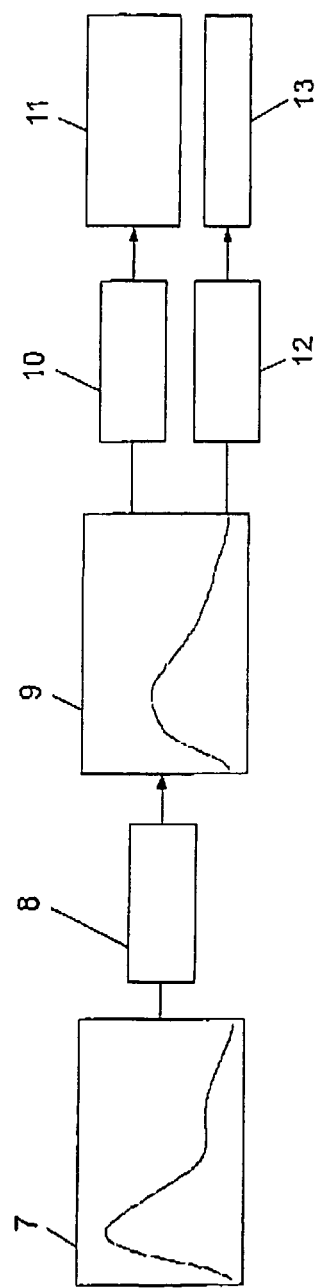
FIG. 2 depicts the structure of the calculation program.

In FIG. 1, the device according to the invention is denoted by 1 and connected with a measuring device 2 that serves to determine the peripheral blood pressure curve. The measuring device 2 is comprised of a sleeve to be, or instance, applied around the upper arm in order to record the peripheral blood pressure curve prevailing there. The respectively measured values are fed to the device 1 via a line 3, and are stored and evaluated there. The device 1 comprises at least one calculation unit, in which the pressure values delivered by the measuring device 2 are subjected to calculation, as schematically illustrated in FIG. 2. The device 1 further comprises an optical display device 4 as well as an input panel 1 and, optionally, keys 6.

FIG. 2 depicts the course of the computational determination of the cardiac output. Departing from the peripheral blood pressure curve 7 detected by the measuring device 2, a central blood pressure curve 9 is calculated by the aid of an artificial neural network 8. From the central blood pressure curve 9, the cardiac output 11 is subsequently calculated utilizing an optimization model 10. Optionally, also the augmentation index 13 can be additionally calculated by the aid of a Spline interpolation 12.

Figure 3:
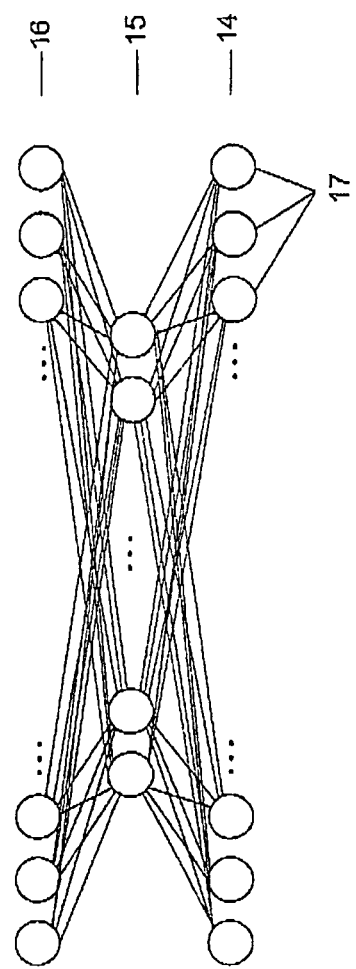
FIG. 3 is a schematic illustration of the artificial neural network employed.

FIG. 3 illustrates the structure of the neural network 8, and it is apparent that the neural network 8 is comprised of three layers 14, 15, 16, the first layer 14 and the last layer 16 being each composed of 100 neurons 17, and the central layer 15 being composed of 10 neurons 17 with a linear transmission function. In the two latter layers 15 and 16, a bias primarily serving to smooth the central pulse curve is each added. The artificial neural network can be implemented by the aid of software, or a hardware-based solution can be applied. In the present case, a software implementation has been chosen.

That is a completely connected feed-forward network without any shortcuts. The weights and the bias for the latter two layers 15 and 16 are determined by supervised learning, the bias of the first layer corresponding to the zero vector.

Departing from the central blood pressure curve determined by the neural network, the cardiac output is determined by the aid of the optimization model 10 as already mentioned. In the present example, the determination of the cardiac output is based on a non-trivial solution of the windkessel equations. The basic idea of this model is that the ejection work of the left heart ventricle follows a defined criterion function. It is departed from an open dynamic system whose system dynamics is described by the windkessel equation:

$$q(t) = R_P C_A \dot{x} + x, \quad (1)$$

wherein $q(t)$ is the aortic root flow, $x(t)$ is the overall blood flow through the periphery of the vascular system, $R_P$ is the peripheral resistance and $C_A$ is the compliance of the arterial system. The following boundary and additional criteria have to be met: The overall blood flow through the periphery of the vascular system at a known period duration ($t_p$) and at a known systole duration ($t_s$) is assumed to be periodic;

$$x(0) = x_0 \quad (2)$$

$$x(t_s) = x_t \quad (3)$$

$$xs = x_0 e^{\frac{(t_p - t_s)}{R_P C_A}} \quad (4)$$

For the aortic root flow, it is required that it becomes zero at the end of the systole:

$$q(t_s) = 0 \quad (5)$$

In addition, it is required that a defined stroke volume (Vs) be pumped and the following relation be met:

$$\int_0^{t_s} q\, dt = V_s \quad (6)$$

$$\int_0^{t_s} x\, dt + \int_{t_y}^{t_p} x\, dt = V_s \quad (7)$$

The approximately exponential drop caused by the flowing off of blood from the arterial windkessel, is approximated by the exponential function $$x_d = x_s e^{\frac{-(t - t_s)}{R_P C_A}} \quad (8)$$

By the aid of an optimization model in regard to the ejection work of the left ventricle, the parameters of interest and the stroke volume are to be calculated from the central pressure curve and with bound estimations for said parameters. This calculation is to be performed by minimizing a deviation measure for the adaptation of the model pressure curve to the pregiven pressure curve.

The algorithm used for the calculation of the parameters and the stroke volume may be described as in algorithm (1). The algorithm is implemented without variation of the parameter $R_C$ in order to reduce the calculation time, and for the parameter a value of 0.01 is assumed. Such a simplification is justifiable on account of the obtained results.

Calculation of the parameters $R_p$, $R_C$ (effective arterial resistance) and $C_A$, and of the stroke volume $V_s$:

Input: central pressure contour
 Output: parameters $R_p$, $R_C$, $C_A$ and stroke volume $V_s$ -continued

```
error_best ← 10e6
for C_A = 0.8 to 1.2 do
    for R_P = 0.8 to 1.5 do
        for R_C = 0.005 to 0.015 do
            calculation of x(t)
            calculation of error:
```

$$\text{Error} = \sum_{i=1}^{N} \left( \frac{p_i^{given} - p_i^{calculated}}{p_i^{given}} \right)^2$$

```
            if Error < Error_best then
                RP_best ← R_p
                RC_best ← R_C
                CA_best ← C_A
                VS_best ← VS
                Error_best ← Error
            end if
        end for
    end for
end for
Return R_p, R_C, C_A and VS
```

The invention claimed is:

1. A method for determining cardiac output from an arterial blood pressure curve measured at a peripheral region, comprising the steps of:
  measuring the arterial blood pressure curve at the peripheral region;
  arithmetically transforming the measured arterial blood pressure curve to an equivalent aortic pressure; and
  calculating the cardiac output from the equivalent aortic pressure, wherein
  the arithmetic transformation of the arterial blood pressure curve measured at the peripheral region into the equivalent aortic pressure is performed by the aid of an artificial neural network having weighting values that are determined by learning.

2. The method according to claim 1, wherein the artificial neural network is configured as a feed-forward network.

3. The method according to claim 1, wherein the artificial neural network is comprised of at least three layers.

4. The method according to claim 1, wherein
  the artificial neural network is comprised of three layers, and
  a number of neurons contained in the first layer and a number of neurons contained in the third layer are each selected to be at least three times a number of neurons contained in the second layer, which is a central layer.

5. The method according to claim 1, wherein
  the artificial neural network is comprised of three layers,
  the first layer and the third layer of the artificial neural network are each composed of at least 100 neurons, and
  the second layer is a central layer and is composed of at least 10 neurons.

6. The method according to claim 1, wherein said learning is performed by supervised learning and the weighting values are determined by the aid of a backpropagation algorithm.

7. The method according to claim 1, wherein the determination of the cardiac output is performed departing from a system dynamics described by a windkessel equation in regard to an optimization of an ejection rate of a left ventricle by applying a variation calculation.

8. The method according to claim 2, wherein the network is a completely connected feed-forward network.

9. The method according to claim 1, wherein
  the artificial neural network is comprised of three layers, and a number of neurons contained in the first layer and a number of neurons contained in the third layer are each selected to be at least five times a number of neurons contained in the second layer, which is a central layer.

10. The method according to claim 1, wherein the artificial neural network is comprised of three layers, and a number of neurons contained in the first layer and a number of neurons contained in the third layer are each selected to be at least ten times a number of neurons contained in the second layer, which is a central layer.

* * * * *